(12) United States Patent
Buysse et al.

(10) Patent No.: US 7,179,258 B2
(45) Date of Patent: Feb. 20, 2007

(54) BIPOLAR ELECTROSURGICAL INSTRUMENT FOR SEALING VESSELS

(75) Inventors: Steven Paul Buysse, Longmont, CO (US); Dale Francis Schmaltz, Fort Collins, CO (US); Robert Luzzi, Boulder, CO (US); Kirk Bryan Olson, Golden, CO (US); Kate Ryland Lawes, Superior, CO (US); Daniel Lee Trimberger, II, Greeley, CO (US); Mathew Erle Mitchell, Boulder, CO (US); Jenifer Serafin Kennedy, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 67 days.

(21) Appl. No.: 10/819,802

(22) Filed: Apr. 7, 2004

(65) Prior Publication Data
US 2004/0225288 A1 Nov. 11, 2004

Related U.S. Application Data

(63) Continuation of application No. 10/090,081, filed on Mar. 1, 2002, now Pat. No. 6,743,229, which is a continuation of application No. 09/502,933, filed on Feb. 11, 2000, now Pat. No. 6,352,536, which is a continuation of application No. 08/968,779, filed on Nov. 12, 1997, now Pat. No. 6,187,003.

(51) Int. Cl.
*A61B 18/18* (2006.01)
(52) U.S. Cl. ............................................... 606/51
(58) Field of Classification Search ............ 606/41–52
See application file for complete search history.

(56) References Cited

U.S. PATENT DOCUMENTS

| 371,664 A | 10/1887 | Brannan et al. |
|---|---|---|
| 702,472 A | 6/1902 | Pignolet |
| 728,883 A | 5/1903 | Downes |
| 1,586,645 A | 6/1926 | Bierman |
| 2,002,594 A | 5/1935 | Wappler et al. |

(Continued)

FOREIGN PATENT DOCUMENTS

| CA | 2104423 | 2/1994 |
|---|---|---|

(Continued)

OTHER PUBLICATIONS

Int'l Search Report EP 05013463.4 dated Sep. 28, 2005.

(Continued)

*Primary Examiner*—Roy D. Gibson

(57) ABSTRACT

A bipolar electrosurgical instrument has opposable seal surfaces on its jaws for grasping and sealing vessels and vascular tissue. Inner and outer instrument members allow arcuate motion of the seal surfaces. An open lockbox provides a pivot with lateral support to maintain alignment of the lateral surfaces. Ratchets on the instrument members hold a constant closure force on the tissue during the seal process. A shank portion on each member is tuned to provide an appropriate spring force to hold the seal surfaces together. During surgery, the instrument can be used to grasp and clamp vascular tissue and apply bipolar electrosurgical current through the clamped tissue. In one embodiment, the seal surfaces are partially insulated to prevent a short circuit when the instrument jaws are closed together. In another embodiment, the seal surfaces are removably mounted on the jaws.

5 Claims, 7 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,176,479 A | 10/1939 | Willis |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,459,187 A | 8/1969 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 4,005,714 A | 2/1977 | Hiltebrandt |
| 4,074,718 A | 2/1978 | Morrison, Jr. |
| 4,088,134 A | 5/1978 | Mazzariello |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Kamiyama et al. |
| 5,176,695 A | 1/1993 | Dulebohn |
| 5,190,541 A | 3/1993 | Abele et al. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A * | 2/1994 | Foshee et al. ............... 606/52 |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,582,611 A | 12/1996 | Tsuruta et al. |
| 5,585,896 A | 12/1996 | Yamazaki et al. |
| 5,590,570 A | 1/1997 | LeMaire, III et al. |
| 5,601,601 A | 2/1997 | Tal et al. |
| 5,603,711 A | 2/1997 | Parins et al. |
| 5,603,723 A | 2/1997 | Aranyi et al. |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |

| Patent No. | Date | Inventor |
|---|---|---|
| 5,658,281 A | 8/1997 | Heard |
| 5,662,667 A | 9/1997 | Knodel |
| 5,667,526 A | 9/1997 | Levin |
| 5,674,220 A | 10/1997 | Fox et al. |
| 5,681,282 A | 10/1997 | Eggers et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,779,701 A | 7/1998 | McBrayer et al. |
| 5,792,137 A | 8/1998 | Carr et al. |
| 5,792,177 A | 8/1998 | Kaseda |
| 5,797,938 A | 8/1998 | Paraschac et al. |
| 5,797,958 A | 8/1998 | Yoon |
| 5,800,449 A | 9/1998 | Wales |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,876,401 A | 3/1999 | Schulze et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,913,874 A | 6/1999 | Berns et al. |
| 5,921,984 A | 7/1999 | Sutcu et al. |
| 5,935,126 A | 8/1999 | Riza |
| 5,944,718 A | 8/1999 | Austin et al. |
| 5,951,549 A | 9/1999 | Richardson et al. |
| 5,954,720 A | 9/1999 | Wilson et al. |
| 5,961,514 A | 10/1999 | Long et al. |
| 5,976,132 A | 11/1999 | Morris |
| 5,984,939 A | 11/1999 | Yoon |
| 5,989,277 A | 11/1999 | LeMaire, III et al. |
| 6,004,335 A | 12/1999 | Vaitekunas et al. |
| 6,010,516 A | 1/2000 | Hulka et al. |
| 6,024,741 A | 2/2000 | Willaimson et al. |
| 6,024,744 A | 2/2000 | Kese et al. |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,066,139 A * | 5/2000 | Ryan et al. .................. 606/50 |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| H1904 H | 10/2000 | Yates et al. |
| 6,126,658 A | 10/2000 | Baker |
| 6,152,923 A | 11/2000 | Ryan |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,322,561 B1 | 11/2001 | Eggers et al. |
| 6,334,860 B1 | 1/2002 | Dorn |
| 6,334,861 B1 | 1/2002 | Chandler et al. |
| 6,350,264 B1 | 2/2002 | Hooven |
| 6,352,536 B1 | 3/2002 | Buysse et al. |
| D457,958 S | 5/2002 | Dycus et al. |
| D457,959 S | 5/2002 | Tetzlaff et al. |
| 6,387,094 B1 | 5/2002 | Eitenmuller |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H * | 7/2002 | Yates et al. .................. 606/51 |
| 6,419,675 B1 | 7/2002 | Gallo, Sr. |
| 6,425,896 B1 | 7/2002 | Baltschun et al. |
| 6,443,970 B1 | 9/2002 | Schulze et al. |
| 6,451,018 B1 | 9/2002 | Lands et al. |
| 6,458,128 B1 | 10/2002 | Schulze |
| 6,458,130 B1 | 10/2002 | Frazier et al. |
| 6,464,704 B2 | 10/2002 | Schmaltz et al. |
| 6,503,248 B1 | 1/2003 | Levine |
| 6,506,189 B1 | 1/2003 | Rittman, III et al. |
| 6,508,815 B1 | 1/2003 | Strul et al. |
| 6,511,480 B1 | 1/2003 | Tetzlaff et al. |
| 6,514,251 B2 | 2/2003 | Ni et al. |
| 6,544,264 B2 | 4/2003 | Levine et al. |
| 6,569,162 B2 | 5/2003 | He |
| 6,585,735 B1 | 7/2003 | Frazier et al. |
| 6,620,161 B2 | 9/2003 | Schulze et al. |
| 6,652,521 B2 | 11/2003 | Schulze |
| 6,682,528 B2 | 1/2004 | Frazier et al. |
| 6,685,724 B1 | 2/2004 | Haluck |
| 6,733,498 B2 | 5/2004 | Paton et al. |
| 6,743,229 B2 | 6/2004 | Buysse et al. |
| D496,997 S | 10/2004 | Dycus et al. |
| D499,181 S | 11/2004 | Dycus et al. |
| 6,926,716 B2 | 8/2005 | Baker et al. |
| 6,929,644 B2 | 8/2005 | Truckai et al. |

| | | | |
|---|---|---|---|
| 6,942,662 B2 | 9/2005 | Goble et al. | |
| 2002/0013583 A1 | 1/2002 | Camran et al. | |
| 2002/0099372 A1 | 7/2002 | Schulze et al. | |
| 2002/0107517 A1 | 8/2002 | Witt et al. | |
| 2002/0111624 A1 | 8/2002 | Witt et al. | |
| 2002/0188294 A1 | 12/2002 | Couture et al. | |
| 2003/0018331 A1 | 1/2003 | Dycus et al. | |
| 2003/0069571 A1 | 4/2003 | Treat et al. | |
| 2003/0078578 A1 | 4/2003 | Truckai et al. | |
| 2003/0139741 A1 | 7/2003 | Goble et al. | |
| 2003/0139742 A1 | 7/2003 | Wampler et al. | |
| 2003/0158549 A1 | 8/2003 | Swanson | |
| 2003/0199869 A1 | 10/2003 | Johnson et al. | |
| 2003/0220637 A1 | 11/2003 | Truckai et al. | |
| 2003/0236325 A1 | 12/2003 | Bonora | |
| 2004/0049185 A1 | 3/2004 | Latterell et al. | |
| 2004/0116979 A1 | 6/2004 | Truckai et al. | |
| 2004/0147925 A1 | 7/2004 | Buysse et al. | |
| 2004/0225288 A1 | 11/2004 | Buysse et al. | |
| 2004/0230189 A1 | 11/2004 | Keppel | |
| 2004/0236325 A1 | 11/2004 | Tetzlaff et al. | |
| 2004/0243125 A1 | 12/2004 | Dycus et al. | |
| 2004/0249371 A1 | 12/2004 | Dycus et al. | |
| 2004/0249374 A1 | 12/2004 | Tetzlaff et al. | |
| 2004/0250419 A1 | 12/2004 | Sremcich et al. | |
| 2004/0254573 A1 | 12/2004 | Dycus et al. | |
| 2005/0004564 A1 | 1/2005 | Wham et al. | |
| 2005/0004568 A1 | 1/2005 | Lawes et al. | |
| 2005/0004570 A1 | 1/2005 | Chapman et al. | |
| 2005/0021025 A1 | 1/2005 | Buysse et al. | |
| 2005/0021026 A1 | 1/2005 | Baily | |
| 2005/0021027 A1 | 1/2005 | Shields et al. | |
| 2005/0033278 A1 | 2/2005 | McClurken et al. | |
| 2005/0101951 A1 | 5/2005 | Wham et al. | |
| 2005/0101952 A1 | 5/2005 | Lands et al. | |
| 2005/0107784 A1 | 5/2005 | Moses et al. | |
| 2005/0107785 A1 | 5/2005 | Dycus et al. | |
| 2005/0113818 A1 | 5/2005 | Sartor et al. | |
| 2005/0113819 A1 | 5/2005 | Wham et al. | |
| 2005/0113826 A1 | 5/2005 | Johnson et al. | |
| 2005/0113827 A1 | 5/2005 | Dumbauld et al. | |
| 2005/0113828 A1 | 5/2005 | Shields et al. | |
| 2005/0119655 A1 | 6/2005 | Moses et al. | |
| 2005/0149151 A1 | 7/2005 | Orszulak et al. | |
| 2006/0079891 A1 | 4/2006 | Arts et al. | |

FOREIGN PATENT DOCUMENTS

| | | | |
|---|---|---|---|
| DE | 2415263 | | 10/1975 |
| DE | 8712328 | | 3/1988 |
| DE | 29616210 | | 1/1997 |
| DE | 19608716 | | 4/1997 |
| DE | 19751108 | | 5/1999 |
| EP | 0364216 | A1 | 4/1990 |
| EP | 518230 | A1 | 12/1992 |
| EP | 0 541 930 | B1 | 5/1993 |
| EP | 0572131 | | 12/1993 |
| EP | 584787 | A1 | 3/1994 |
| EP | 0623316 | A1 | 11/1994 |
| EP | 0624348 | A2 | 11/1994 |
| EP | 0650701 | A1 | 5/1995 |
| EP | 0754437 | A3 | 3/1997 |
| EP | 0694290 | A3 | 3/1998 |
| EP | 0717966 | A1 | 6/1998 |
| EP | 853922 | A1 | 7/1998 |
| EP | 0875209 | A1 | 11/1998 |
| EP | 0878169 | A1 | 11/1998 |
| EP | 0887046 | A3 | 1/1999 |
| EP | 0923907 | A1 | 6/1999 |
| EP | 0986990 | A1 | 3/2000 |
| EP | 1034747 | A1 | 9/2000 |
| EP | 1034748 | A1 | 9/2000 |
| EP | 1025807 | A3 | 10/2000 |
| EP | 1034746 | A3 | 10/2000 |
| EP | 1050278 | A1 | 11/2000 |
| EP | 1053719 | A1 | 11/2000 |
| EP | 1053720 | A1 | 11/2000 |
| EP | 1055399 | A1 | 11/2000 |
| EP | 1055400 | A1 | 11/2000 |
| EP | 1080694 | A1 | 3/2001 |
| EP | 1082944 | A1 | 3/2001 |
| EP | 1159926 | A2 | 12/2001 |
| EP | 1330991 | A1 | 7/2003 |
| EP | 1486177 | A2 | 6/2004 |
| EP | 1532932 | A1 | 5/2005 |
| GB | 2214430 | A | 6/1989 |
| JP | 501068 | | 9/1984 |
| JP | 502328 | | 3/1992 |
| JP | 5-40112 | | 2/1993 |
| JP | 06343644 | A2 | 12/1994 |
| JP | 07265328 | A2 | 10/1995 |
| JP | 08056955 | A2 | 3/1996 |
| JP | 08252263 | A2 | 10/1996 |
| JP | 09010223 | A2 | 1/1997 |
| JP | 11244298 | A2 | 9/1999 |
| JP | 2000342599 | A2 | 12/2000 |
| JP | 2000350732 | A2 | 12/2000 |
| JP | 2001008944 | A2 | 1/2001 |
| JP | 2001029356 | A2 | 2/2001 |
| JP | 2001128990 | A2 | 5/2001 |
| SU | 401367 | | 10/1973 |
| SU | 401367 | | 11/1974 |
| WO | WO 92/06642 | | 4/1992 |
| WO | WO 94/08524 | A | 4/1994 |
| WO | WO 95/02369 | | 1/1995 |
| WO | WO 95/07662 | | 3/1995 |
| WO | WO 96/022056 | | 7/1996 |
| WO | WO 96/13218 | | 9/1996 |
| WO | WO 97/00646 | | 1/1997 |
| WO | WO 97/00647 | | 1/1997 |
| WO | WO 97/10764 | | 3/1997 |
| WO | WO 97/24073 | | 7/1997 |
| WO | WO 97/24993 | | 7/1997 |
| WO | WO 98/27880 | | 7/1998 |
| WO | WO 99/03407 | | 1/1999 |
| WO | WO 99/03408 | | 1/1999 |
| WO | WO 99/03409 | | 1/1999 |
| WO | WO 99/12488 | A | 3/1999 |
| WO | WO 99/40857 | | 8/1999 |
| WO | WO 99/040861 | | 8/1999 |
| WO | WO 99/51158 | | 10/1999 |
| WO | WO 99/066850 | | 12/1999 |
| WO | WO 99/66850 | A | 12/1999 |
| WO | WO 00/24330 | | 5/2000 |
| WO | WO 00/24331 | | 5/2000 |
| WO | WO 00/41638 | | 7/2000 |
| WO | WO 00/53112 | | 9/2000 |
| WO | WO 01/17448 | A | 3/2001 |
| WO | WO 01/54604 | | 8/2001 |
| WO | WO 02/07627 | | 1/2002 |
| WO | WO 02/080783 | | 10/2002 |
| WO | WO 02/080784 | | 10/2002 |
| WO | WO 02/080785 | | 10/2002 |
| WO | WO 02/080786 | | 10/2002 |
| WO | WO 02/080793 | | 10/2002 |
| WO | WO 02/080794 | | 10/2002 |
| WO | WO 02/080795 | | 10/2002 |
| WO | WO 02/080796 | | 10/2002 |
| WO | WO 02/080796 | A1 | 10/2002 |
| WO | WO 02/080797 | | 10/2002 |
| WO | WO 02/080798 | | 10/2002 |
| WO | WO 02/080799 | | 10/2002 |
| WO | WO 02/081170 | | 10/2002 |
| WO | WO 03/101311 | | 12/2003 |
| WO | WO 04/032777 | | 4/2004 |
| WO | WO 2004/052221 | A1 | 6/2004 |

| WO | WO 04/073490 | 9/2004 |
| --- | --- | --- |
| WO | WO 04/082495 | 9/2004 |
| WO | WO 2004/082495 A1 | 9/2004 |
| WO | WO 2004/098383 A1 | 11/2004 |
| WO | WO 04/103156 | 12/2004 |

OTHER PUBLICATIONS

Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectomy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.
"Innovations in Electrosurgery" Sales/Product Literature.
LigaSure Vessel Sealing System, the Seal of Confidence in General, Gynecologic, Urologic, and Laparaoscopic Surgery Sales/Product Literature.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC.
"Reducing Needlestick Injuries in the Operating Room" Sales/Product Literature.
Chung et al., "Clinical Experience of Sutureless Closed Hemorrhoidectomy with LigaSure" Diseases of the Colon & Rectum vol. 48, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, ☐Apr. 2001 pp. 236-237.
W. Scott Helton, "LigaSure Vessel Sealing System: Revolutionary Hemostasis Product for General Surgery" Sales/Product Literature.
Michael Choti, "Abdominoperineal Resection with the LigaSure Vessel Sealing System and LigaSure Atlas 20 cm Open Instrument" Innovations That Work, ☐Jun. 2003.
Craig Johnson, "Use of the LigaSure Vessel Sealing System in Bloodless Hemorrhoidectomy" Innovations That Work, ☐Mar. 2000.
Muller et al., "Extended Left Hemicolectomy Using the LigaSure Vessel Sealing System" Innovations That Work,☐Sep. 1999.
Herman et al., "Laparoscopic Intestinal Resection With the LigaSure Vessel Sealing System: A Case Report" Innovations That Work,☐Feb. 2002.
Carus et al., "Initial Experience With The LigaSure Vessel Sealing System in Abdominal Surgery" Innovations That Work,☐Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3.
E. David Crawford "Use of a Novel Vessel Sealing Technology in Management of the Dorsal Veinous Complex" Sales/Product Literature.
Jarrett et al., "Use of the LigaSure Vessel Sealing System for Peri-Hilar Vessels in Laparoscopic Nephrectomy" Sales/Product Literature.
E. David Crawford "Evaluation of a New Vessel Sealing Device in Urologic Cancer Surgery" Sales/Product Literature.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature.
Johnson et al. "Evaluation of a Bipolar electrothermal Vessel Sealing Device in Hemorrhoidectomy" Sales/Product Literature.
Int'l Search Report PCT/US01/11218.
Int'l Search Report PCT/US99/24869.
Int'l Search Report PCT/US98/18640.

Int'l Search Report PCT/US98/23950.
PCT/US01/11340, International Search Report.
PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.

EP 98944778, International Search Report.
EP 98958575, International Search Report.
EP 04027479, International Search Report.
EP 04027705, International Search Report.
EP 04027314, International Search Report.
US 6,663,629, 12/2003, Buysse et al. (withdrawn)

* cited by examiner

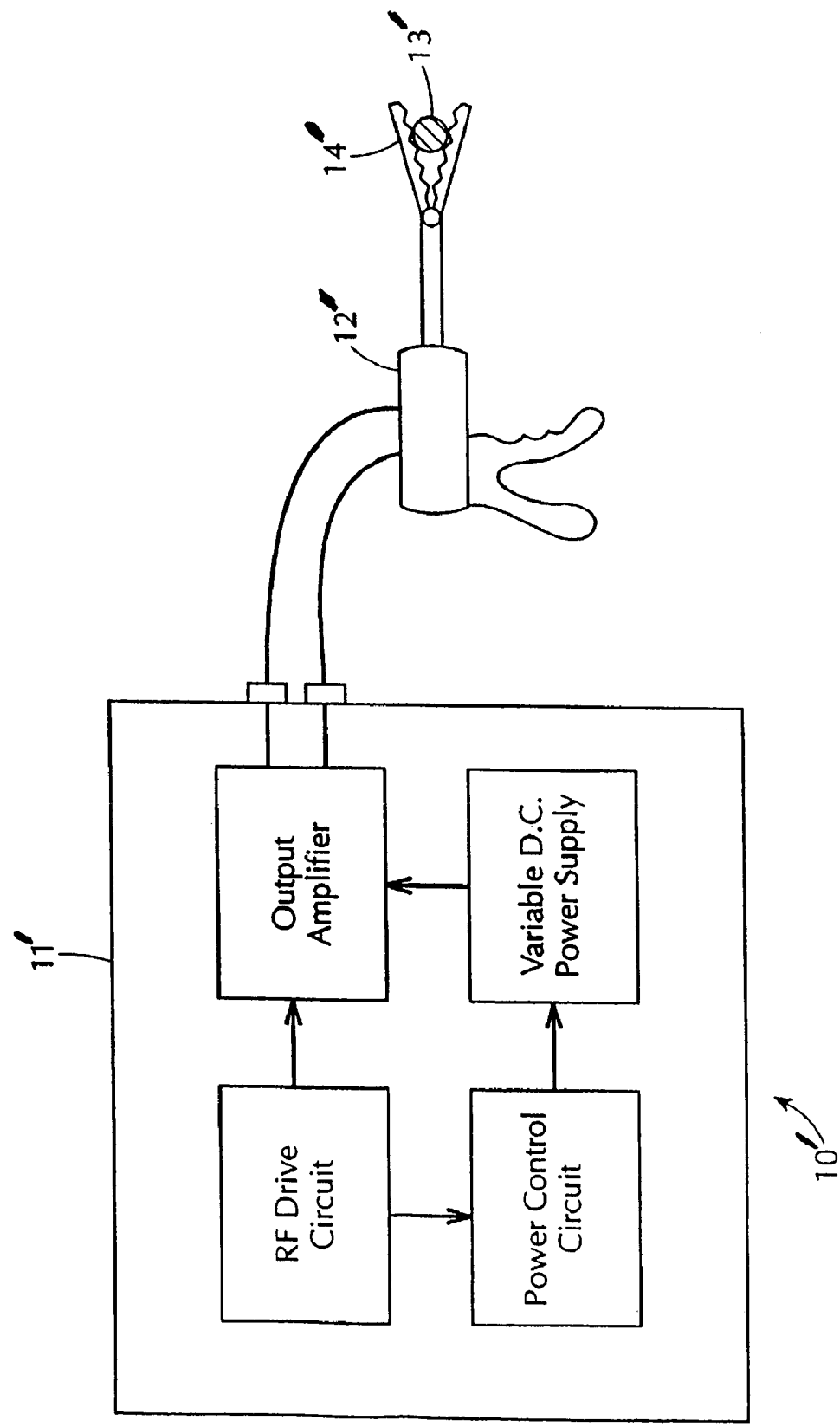

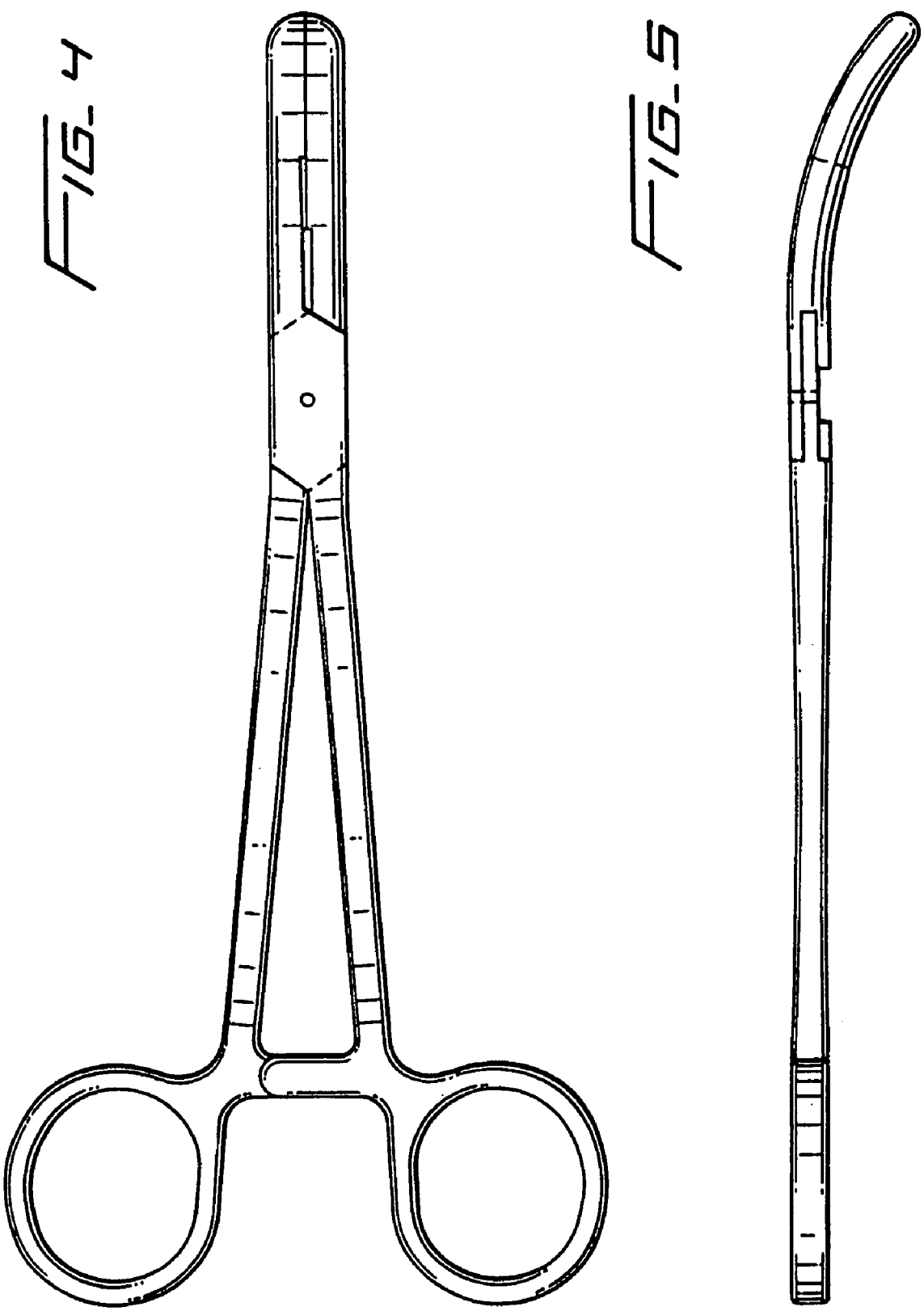

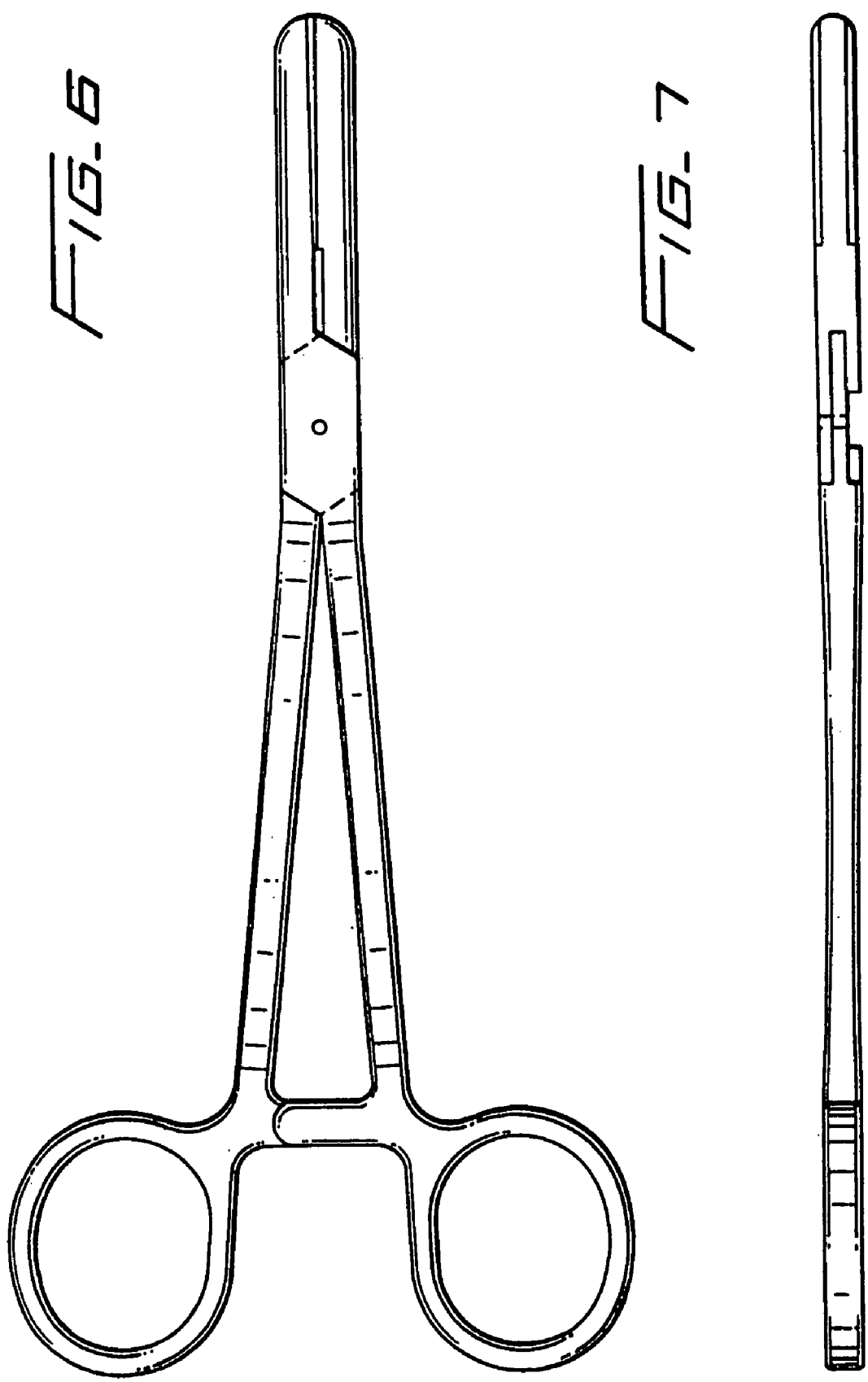

BIPOLAR ELECTROSURGICAL INSTRUMENT FOR SEALING VESSELS

CROSS REFERENCE TO RELATED APPLICATIONS:

This application is a continuation of U.S. patent application Ser. No. 10/090,081 (now U.S. Pat. No. 6,743,229) filed on Mar. 1, 2002, which is a continuation of U.S. patent application Ser. No. 09/502,933 (now U.S. Pat. No. 6,352,536) filed on Feb. 11, 2000, which is a continuation of U.S. patent application Ser. No. 08/968,779 (now U.S. Pat. No. 6,187,003) filed on Nov. 12, 1997, the entire contents of all of which being incorporated by reference herein.

FIELD OF THE INVENTION

This invention relates to an electrosurgical instrument for permanently closing vessels in a human or animal, and more particularly to a bipolar electrosurgical instrument that seals vessels and vascular tissue by applying a combination of pressure and electrosurgical current.

BACKGROUND OF THE DISCLOSURE

A hemostat is commonly used in surgical procedures to grasp, dissect and clamp tissue. It is typically a simple pliers-like tool that uses mechanical action between its jaws to constrict vessels without cutting them. It is also typical for hemostats to have an interlocking ratchet between the handles so that the device can be clamped and locked in place.

Many hemostats are used in a typical open-surgical procedure. Once vascular tissue has been clamped with a hemostat, it is common for a surgeon to tie a suture around the tissue to close it off permanently prior to removing the hemostat. Several hemostats may be left in the surgical field until the surgeon has the opportunity to tie a suture around each section of clamped tissue.

Small blood vessels have been closed using electrosurgical instruments without the need for sutures. For example, neurosurgeons have used bipolar instruments to coagulate vessels in the brain that are smaller than two millimeters in diameter. These bipolar instruments are typically tweezers-like devices with two arms that can be deflected toward each other to grasp tissue. However, it has been found that these instruments are not capable of sealing blood vessels with diameters larger than about two millimeters. There has been a long-felt need for an easy way to seal larger vessels and vascular tissue bundles without the need for sutures.

It is thought that the process of coagulating small vessels is fundamentally different than vessel sealing. Coagulation is defined as a process of desiccating tissue wherein the tissue cells are ruptured and dried. Vessel sealing is defined as the process of liquefying the collagen in the tissue so that it crosslinks and reforms into a fused mass. Thus, coagulation of small vessels is sufficient to permanently close them. Larger vessels need to be sealed to assure permanent closure.

A number of bipolar electrosurgical forceps and clamps are known in the field. However, these instruments are not designed to apply the correct pressure to a blood vessel to achieve a lasting seal. All of these instrument also suffer from the drawback that they do not combine the simplicity and familiarity of a hemostat with a bipolar electrosurgical circuit.

An example of a bipolar electrosurgical power curve for vessel sealing is disclosed in a U.S. patent application entitled, "Energy Delivery System for Vessel Sealing," Ser. No. 08/530,495, filed Sep. 19, 1995, and is hereby incorporated by reference and made a part of this disclosure.

A U.S. patent application entitled, "Vascular Tissue Sealing Pressure Control and Method," Ser. No. 08/530,450, filed on Sep. 19, 1995, discloses another surgical tool for sealing vessels, and is hereby incorporated by reference and made a part of this disclosure.

One of the important advances of the present system is that it can effectively seal larger vessels of a patient without leaving any foreign material in the body of the patient. The present system is capable of sealing vessels as large as ten millimeters in diameter. Another advantage of the present system is that the surgeon can visually inspect the integrity of the seal.

This invention works with a combination of pressure and controlled application of electrosurgical energy to achieve the desired result. Therefore, the system requires a tool to grasp and apply an appropriate amount of pressure to the tissue of the patient. The term "pressure" refers to the closure force on the vessels or other tissue that is applied by the end effectors of the tool. The tool must also be capable of conducting electrosurgical energy to the tissue concurrently with the application of pressure.

An electrosurgical generator is used to generate the electrosurgical energy. The electrosurgical energy is preferably applied in a specified manner by using an automatic control system. The control system regulates the output current and the output voltage of the electrosurgical generator in a manner that provides optimal vessel sealing.

One of the advances of the present invention is that a high current is applied to the tissue in order to melt the proteins. The high current is important for its effect on the tissue. Similarly, the output voltage is regulated to reduce sparking and localized tissue heating. The voltage is preferably kept below one hundred sixty volts RMS, and in the preferred embodiment is kept below one hundred twenty volts RMS.

Earlier attempts to seal vessels with electrosurgery were unsuccessful in part because a relatively low current was applied. The present invention may draw a maximum current in excess of two amperes RMS through the tissue. This level of output current is higher than the design capabilities of many presently available electrosurgical generators.

Charring of the tissue can be avoided by terminating the flow of electrosurgical energy to the tissue at an appropriate time. There are several techniques for determining when to terminate the electrosurgical energy. One technique is to monitor the impedance of the output load on the electrosurgical generator. When the impedance reaches a certain level, preferably above one thousand ohms, the electrosurgical energy should be terminated.

Another technique is to monitor the phase angle between the output voltage and the output current. Energy delivery to the surgical tool should be terminated preferably when the output current leads the output voltage by an angle greater than approximately fifty degrees.

A third technique for determining when to terminate the electrosurgical energy is to monitor the output current. As the tissue desiccates, the amount of electrical current flowing through the tissue decreases. The generator may terminate the energy delivery to the surgical tool when the output current drops below approximately 200 milliamperes RMS.

It is preferable to maintain pressure on the vessels or tissue of the patient for a short time after the electrosurgical energy has been substantially terminated. This allows the tissue to cool in its newly sealed state. An audible tone indicator in the generator is preferably available to indicate to the surgeon when it is appropriate to release the pressure on the tissue. The time delay may be up to five seconds after terminating the energy delivery to the surgical tool.

In the preferred embodiment there are four main steps for using the tissue sealing system. The first step may include applying and maintaining pressure on the tissue. The second step may include rapidly heating the tissue with electrosurgical energy. The third step may include lowering the energy which is delivered to the tissue so that the tissue will desiccate without charring. The final step may include terminating the electrosurgical energy delivery to the tissue so that the tissue is allowed to cool while still under pressure.

An automatic control system is preferably located within the electrosurgical generator and has, as one of its functions, the ability to automatically transition through the different levels of electrosurgical energy delivery. In an alternative embodiment, the power delivery to the surgical tool may not have discrete, step-wise levels. Instead, the power delivery may be a smooth function which initially delivers a high current, and then transitions to a lower power lever to desiccate the tissue, followed by termination of the power delivery when the impedance of the tissue rises above approximately one thousand ohms.

What follows is a summary of the various embodiments of the invention. The preferred embodiment of the electrosurgical energy delivery system is used for sealing vessels and other tissues of a patient. The system comprises a generator, a surgical tool, and means for controlling the level of electrosurgical energy which is delivered to the tissue.

The generator is preferably capable of delivering a controlled level of high frequency electrosurgical energy. The output of the generator may be characterized as having an output voltage and an output current which are each regulated in the preferred embodiment. The generator in the present system could limit the output voltage to a value below one hundred sixty volts RMS, and most preferably would be limited below one hundred twenty volts RMS. One of the reasons for limiting the output voltage is to avoid sparks and arcing which cause local high temperature zones in the tissue, and can also result in the tissue sticking to the electrodes. Another disadvantage of arcing is that it may result in transection of the vessel.

The surgical tool is most preferably connected to the generator output for receiving the electrosurgical energy. The surgical tool may take the form of forceps, clamps, or any instrument with articulating members for grasping tissue.

In a bipolar configuration, one member of the surgical tool will be electrically connected to be an active electrode, and another member of the surgical tool will be electrically connected to be a return electrode. Alternatively, in a monopolar arrangement, the surgical tool may be electrically connected to only one electrical pole of the generator, while the patient is electrically connected to the other electrical pole. While the members are grasping tissue, electrosurgical energy from the generator will flow in circuit through the tissue.

In the preferred embodiment, there are means for controlling the level of electrosurgical energy delivered to the surgical tool. The level of electrosurgical energy is controlled such that the vessels and other tissues are sealed as they are grasped by the members of the surgical tool. The level of electrosurgical power may refer to the RMS power output of the generator, which may be a function of output voltage, output current, frequency, and duty cycle.

The surgical tool may also have means for applying pressure to the vessels and other tissues between the members concurrently with the application of the electrosurgical energy. The pressure application means can take of the form of a latch or indent which holds a known spring force against the members of the tool. There may be several selectable levels of pressure available from the surgical tool. For example, it may be desirable to apply a high level of pressure to arteries and vascular tissue, and a lower level of pressure to veins.

During an operation, the surgeon may grasp a vessel with the surgical tool and operate the mechanisms on the tool to apply the desired level of pressure to the vessel. Once the pressure has been applied to the vessel, the surgeon may activate the electrosurgical energy. The generator applies the appropriate amount of electrosurgical energy according to a specified power curve.

There are several methods for feedback control to the generator. Feedback control is important because the transition points in the power curve are scheduled to occur according to the state of the tissue. In addition, it would be undesirable to apply too much energy to the tissue and thus cause charring and sticking. Several parameters may be monitored for purposes of feedback control. These parameters include the impedance of the tissue, the phase angle between the output voltage and output current, the level of output current flowing through the tissue, and the temperature of the tissue.

It is preferable for the generator to have means for at least approximating impedance of the vessels and other tissues of the patient as they are grasped by the members of the surgical tool. For example, one way to approximate the impedance of the tissue is to assume that the impedance is mostly resistive, and thus make the approximation by dividing the output voltage by the output current. Other numerical techniques for approximating impedance are available so that a long division need not be performed. One such approximation technique is to scale the output voltage and output current appropriately so that a range of impedance may be estimated by mere comparison and bit shifting in a digital circuit.

Impedance of the tissue is a good indicator of the state of desiccation of the tissue. One reason for having an estimate of the impedance is to control the level of electrosurgical energy so that it is substantially terminated when the impedance of the vessels and other tissues rises above approximately one thousand ohms. In certain embodiments of the invention, it may be convenient to terminate the energy delivery to the surgical tool when the estimate of impedance rises above 2048 ohms.

The preferred means for controlling the level of electrosurgical energy comprises several stages. The first stage is a rapid power delivery function for rapidly increasing the power delivery to the vessels and other tissues until a first impedance breakpoint is reached. The second stage is a constant power delivery function for maintaining a constant power delivery to the vessels and other tissues until proteins in the vessels and other tissues have melted. The third stage is a low power delivery function for maintaining a low power delivery to the vessels and other tissues until a second impedance breakpoint is reached. In the preferred embodiment, the transitions between the stages are executed automatically in the generator without further input from the surgeon. The impedance breakpoints are preferably 16 ohms for the first breakpoint, and 2048 ohms for the second breakpoint.

A method for sealing vessels and other tissues of a patient is also claimed. The method comprises the steps of: applying pressure to the vessels and other tissues of the patient; applying a first level of electrosurgical energy to the vessels and other tissue sufficient to melt proteins in the tissue; applying a second level of electrosurgical energy to the vessels and other tissue sufficient to cause desiccation without charring; reducing the electrosurgical energy substantially for a length of time sufficient to allow the vessels and other tissues to cool into a new compressed form; and relieving the pressure on the tissue. The step of relieving the pressure on the tissue may occur after a delay of less than five seconds. Additionally, there may be a step of creating an audible indication after the delay is over.

An additional step in the method may be approximating impedance of the vessels and other tissues. If this step is carried out, there may be another step of terminating the second level of electrosurgical energy after the impedance of the vessels and other tissues rises above approximately one thousand ohms.

FIG. 1' is a schematic diagram of an electrosurgical vessel sealing system.

FIG. 2' is a set of power curves which represent the electrosurgical power delivered to the tissue as a function of the tissue impedance.

An electrosurgical energy delivery system 10' is shown in FIG. 1'. The system 10' is used for sealing vessels and other tissues of a patient 13', including ducts, veins, arteries, and vascular tissue. The system 10' comprises an electrosurgical generator 11', a surgical tool 12', and means to control the output of the electrosurgical generator 11' such that it works cooperatively with the surgical tool 12' to effectively seal vessels and other tissues of a patient 13'.

The electrosurgical generator 11' must be capable of delivering a controlled level of electrosurgical output power. The output power may be controlled by adjusting the output current and the output voltage. The surgical tool 12' is electrically connected to the generator 11' for receiving the electrosurgical power. The surgical tool 12' has members 14', or end effectors, capable of grasping the vessels and other tissues of the patient 13'. The members 14' are also capable of applying and maintaining a relatively constant level of pressure to the vessel.

The electrosurgical generator 11' must have means for automatically controlling the level of electrosurgical power delivered to the surgical tool 12'. This can be in the form of a feedback control system. In the preferred embodiment, there are also circuits for limiting the output current and the output voltage. In one embodiment, an adjustable high voltage power supply is used to adjust an RF output stage for controlling the electrosurgical output.

The power output of the generator 11' is described in terms of a power curve, and a preferred embodiment is shown in FIG. 2'. The power curve may be described in terms of several stages. The stages may be discrete, or may be approximated by a smooth continuous function. In the first stage of the power curve, the electrosurgical generator 11' delivers output power even at impedances below approximately sixteen ohms, and holds a high power lever until the proteins in the tissue have sufficiently melted. During this first stage, the output current is allowed to increase to a maximum amplitude which is typically greater than two amperes RMS. It has been found that a high current is important for effective vessel sealing.

After the first stage, the electrosurgical power is lowered to a level sufficient to desiccate the vessels and other tissues. The lower power enables the desiccation to occur without charring the tissue.

A final stage involves allowing the tissue to cool into its new sealed form. During this final stage, the application of electrosurgical power to the tissue is substantially terminated. After the tissue has cooled, the closure force is released. The length of time for cooling is typically less than five seconds. In the preferred embodiment, a audible tone would indicate to the surgeon that the sealing process was complete. The surgeon would thereafter release the vessel from the surgical tool 12'.

It is thought that the initial high current causes proteins in the tissue to melt. The subsequent lower power delivery to the tissue allows the proteins to cross link. As the tissue cools, the new cross linked tissue will form a permanent seal of the vessel.

The surgical tool 12' may further comprise an index for selectively applying multiple levels of closure force between the members 14'. For example, arteries will require a greater closure force than veins. It has been found that a closure force of greater than 1500 grams is effective for sealing arteries. A closure force of less than 500 grams is effective for sealing veins.

In the preferred embodiment, the surgical tool 12' will have a spring that compresses to hold a closure force on the members 14'. The index is mechanically linked to the spring such that each successive stop on the index holds a higher compression on the spring. The spring will not begin to compress until the members 14' encounter resistance to closure.

In the preferred embodiment, the generator 11' further comprises means for approximating impedance of the vessels and other tissues of the patient 13' as they are grasped by the members 14' of the surgical tool 12'. The calculation of impedance can require long division and other lengthy mathematical manipulations. There are a variety of techniques for making a quick approximation of impedance which would be sufficient for purposes of controlling the power output of the electrosurgical generator 11'. For example, comparison of the output voltage with the output current can yield an estimate of the impedance without resorting to long division.

The impedance of the tissue gives an indication of the state of desiccation of the tissue. By monitoring impedance, the generator 11' can provide the appropriate amount of electrosurgical energy without charring the tissue. For example, the power control circuit includes a power cutoff function for substantially terminating the power delivery to the surgical tool 12' when the impedance of the vessels and other tissues rises above approximately one thousand ohms.

The power control curves shown in FIG. 2' represent the electrosurgical output of the generator 11' as a function of tissue impedance. At low impedances, the electrosurgical power is increased by rapidly increasing the output current, as shown by the segment labeled A. The increase in electrosurgical power is terminated after a first impedance breakpoint is reached. The first impedance breakpoint is shown as Point 1 in FIG. 2'. In the preferred embodiment, this point is typically below 20 ohms.

Next, the electrosurgical power is held approximately constant until proteins in the vessels and other tissues have melted. The impedance at which this segment ends will vary in accordance with the magnitude of the RMS power. Thus, where the maximum RMS power is approximately 125 Watts, this segment will end at approximately 128 ohms.

This is shown as the segment labeled B in FIG. 2'. Where a lower power is used, such as 75 Watts, the segment may end at 256 ohms. This is shown as the segment labeled C in FIG. 2'.

Next, the output power is lowered to less than half of its maximum value. The low power delivery is terminated when a second impedance breakpoint is reached. In the preferred embodiment, the second breakpoint is approximately at 2048 ohms.

As an alternative to using impedance to determine the second breakpoint, the phase angle between current and voltage may be used. In this alternative embodiment, the generator 11' includes means for substantially terminating the power delivery to the surgical tool 12' when the output current leads the output voltage by an angle greater than approximately fifty degrees.

In yet another alternative embodiment, the generator 11' will terminate the power delivery to the surgical tool 12' when the output current drops below approximately 200 milliamperes RMS.

It is desirable to have the generator 11' limit its output voltage at all times to less than one hundred sixty volts RMS. The reason for keeping the output voltage low is to prevent arcing and the resulting localized tissue burn spots which might cause the tissue seal to fail.

A method for sealing vessels and other tissues of a patient 13' comprises the following steps. First, apply a closure force to the vessels and other tissues of the patient 13' sufficient to substantially close off the interior passages of the vessels or tissue. Second, apply a first level of electrosurgical power to the vessels and other tissues, wherein the peak output current is greater than two amperes and the peak output voltage is less than one hundred sixty volts RMS. Third, reduce the electrosurgical power to a second level which is less than half of the first level. Fourth, apply the second level of electrosurgical power to the vessels and other tissue of the patient 13' for a length of time sufficient to cause desiccation without charring. Fifth, reduce the electrosurgical power substantially for a length of time sufficient to allow the vessels and other tissues to cool into a new compressed form. Sixth, relieve the closure force on the tissue.

The fifth step of reducing the electrosurgical power can be accomplished either by terminating the power to the surgical tool 12', or by reducing the power to the surgical tool 12' to a very low level. In one embodiment, the electrosurgical energy would be terminated completely so that the tissue 13' would cool in the fastest time possible. In an alternative embodiment, the generator 11' would continue to output approximately one watt of power for the purpose of maintaining a closed circuit with the tissue 13' until the tissue has cooled into its compressed form.

In the preferred embodiment, the method for sealing vessels and other tissues will have the additional step of periodically approximating the impedance of the vessels and other tissues. This step will enable a control system in the generator 11' to adjust the output power in accordance with the impedance of the tissue. For example, the step of applying a second level of electrosurgical power would be terminated after the impedance of the vessels and other tissues rises above approximately one thousand ohms.

Alternatively, the step of substantially terminating the power delivery to the surgical tool 12' can occur when the output current leads the output voltage by an angle greater than approximately fifty degrees. An additional alternative is to terminate the power delivery to the surgical tool 12' when the output current drops below approximately 200 milliamperes RMS.

In the preferred embodiment, there are additional steps of limiting the output voltage to a value below approximately one hundred sixty volts RMS, and audibly indicating when the closure force on the vessels and other tissues should be removed. The audible indication occurs after substantially reducing the level of electrosurgical power, and after a further delay of less than five seconds.

U.S. Pat. No. 371,664 discloses a pair of electric forceps with positive and negative electric poles located on the jaws.

U.S. Pat. No. 728,883 discloses an electrothermic instrument in which electricity is used to heat one of the jaws of the instrument.

U.S. Pat. No. 1,586,645 discloses a bipolar instrument for coagulating tissue.

U.S. Pat. No. 2,002,594 discloses a bipolar laparoscopic instrument for treating tissue, whereby coagulation and cutting of tissue can be performed with the same instrument.

U.S. Pat. No. 2,176,479 discloses an instrument for finding and removing metal particles. The jaws of the instrument are designed to complete an electrical circuit when conductive material is placed therebetween. An insulated pivot and an insulated ratchet are used to prevent a short circuit.

U.S. Pat. No. 3,651,811 discloses a bipolar electrosurgical instrument for cutting and coagulating tissue.

U.S. Pat. No. 4,005,714 discloses bipolar coagulation forceps with jaws that open and close by way of an actuating sleeve.

U.S. Pat. Nos. 4,370,980 and 5,116,332 disclose an electrocautery hemostats wherein the hemostatic clamping function and the electrocautery function may be accomplished with a single instrument. Monopolar electrosurgical designs are shown and described.

U.S. Pat. No. 4,552,143 discloses a family of removable switch electrocautery instruments, including an electrocautery hemostat. Monopolar electrosurgical designs are shown and described.

U.S. Pat. No. 5,026,370 discloses an electrocautery forceps instrument having an enclosed electrical switching mechanism. Monopolar electrosurgical designs are shown and described.

U.S. Pat. No. 5,443,463 discloses coagulating forceps having a plurality of electrodes.

U.S. Pat. No. 5,484,436 discloses bipolar electrosurgical instruments for simultaneously cutting and coagulating tissue.

The article, "The Mechanism of Blood Vessel Closure by High Frequency Electrocoagulation" discloses experiments upon the blood vessels of dogs. The sentence starting on the last line of page 823 describes "an electrode forceps, each of the blades being insulated form the other and each connected to a terminal of the high frequency generator."

The article, "Studies on coagulation and development of an automatic computerized bipolar coagulator" discloses on page 150 that, "It was not possible to coagulate safely arteries with a diameter larger than 2 to 2.5 mm." On page 151, line 5, it is noted that "Veins can be coagulated safely up to a diameter of 3 to 4 mm."

Russian Patent 401,367 discloses a bipolar instrument with a linkage that brings the working jaws together in a parallel manner.

Prior disclosures have not provided a design for a bipolar electrosurgical instrument capable of conveniently applying a constant pressure, from a calibrated spring-loaded source held by a ratchet, that is sufficient to seal vessels and vascular tissue.

SUMMARY OF THE INVENTION

It is the general objective of this invention to provide a bipolar electrosurgical instrument that can fuse tissue without the need for a suture or surgical clips. The instrument conducts electrosurgical current between two seal surfaces located on opposable jaws. The electrosurgical current passes through tissue clamped between the jaws and remolds the collagen to fuse the tissue and form a permanent seal.

One advantage of the invention is that blood vessels can be quickly fused and permanently sealed against passage of blood or other fluids. The instrument thereby reduces operating-room time, provides improved access to target tissues, and increases the efficiency of the surgical procedure.

Another advantage is that no sutures or staples are required to permanently seal blood vessels, and no foreign material is left in the body of the patient.

Yet another advantage is that vessels can be sealed as the instrument is applied, and then the instrument can be removed from the surgical field. This keeps the surgical field clear of extraneous tools that may hinder the surgeon's access to the surgical site.

Yet another advantage is that the proper amount of pressure can be applied by the instrument to the vessel or vessels, thereby increasing the likelihood of a successful surgical outcome.

The bipolar electrosurgical instrument of the present invention comprises inner and outer members connected by an open lockbox, interlocking ratchet teeth, and electrical terminals with conductive pathways leading to seal surfaces. The inner and outer members each have a ring handle near a proximal end and an opposable seal surface near a distal end. The proximal end is held and controlled by the surgeon, while the distal end is used to manipulate tissue. The open lockbox joins the inner and outer members to allow arcuate motion of each opposable seal surface. The open lockbox is generally designed to provide lateral support so that both seal surfaces move in approximately the same plane. The seal surfaces are preferably aligned opposite each other when the instrument jaws are closed together. To provide lateral support, the open lockbox comprises a pivot and at least one flange extending over the inner member and attached to the outer member.

The instrument is tuned to provide a proper closure force by adjusting the dimensions of a shank portion on each of the inner and outer members. The shank portion is defined as the portion of each member bounded by its respective ratchet stub and the open lockbox. During use, the surgeon squeezes the ring handles to compress tissue between the seal surfaces. The shank portion of each member flexes in the manner of a cantilever spring, and can be locked in a deflected position with the ratchet to hold a constant force. It is one of the objects of the invention to provide a range of ratchet stops that correspond to a range of appropriate closure forces on the seal surfaces of the instrument.

Ratchet teeth are located on each member near the ring handle. The ratchet teeth are generally designed to interlock against the spring force from the shanks. The spring force is thus transmitted through the pivot to hold the seal surfaces against each other. A range of closure forces is required in an instrument, depending on the type and thickness of the tissue to be sealed. It is thus desirable to have several ratchet stops, each providing a progressively larger force to the seal surfaces.

An electrical connector is located on each ring handle. The electrical connector may be a metal post that is integrally formed with the member and ring handle. Bipolar electrical cables from an electrosurgical generator are connected to the instrument at the electrical connectors. An electrically conductive path on each of the inner and outer members conducts the electrosurgical current to the seal surfaces. The electrically conductive path may be along the stainless steel members. An electrically insulative coating is preferably bonded to the outer surfaces of the members to protect the surgeon and patient against inadvertent electrical burns.

The following terms are herein defined as follows. The applied force of the instrument is the total force being applied to the tissue between the jaws. The jaws are the members near the distal end of the instrument, from the lockbox to the tip of the instrument. The electrodes are the metal surfaces that conduct electricity to the tissue. The seal surface is the feature on the electrode that comes in direct contact with the tissue. The shank is the portion of each member between the lockbox and the ratchet. The ring handles are the elements on the members, near the proximal end of the instrument, that are grasped by the surgeon. The lockbox is the structure that allows the members to pivot, including the pivot pin and other cooperating surfaces. The inner member is the member that is generally captured in the interior of the lockbox. The outer member is the member that is on the outside of the lockbox. Electrode pressure is calculated by dividing the applied force over the complete area of the seal surface. Tissue pressure is calculated by dividing the applied force over the area of tissue placed between the jaws.

It has been found through experimentation that an instrument for vessel fusion (also referred herein as vessel sealing) should compress the tissue with a proper amount of pressure between the instrument jaws. The pressure is preferably sufficient to close any blood-carrying lumen. The pressure is preferably low enough so that the tissue is not split apart within the instrument jaws.

The jaws of the instrument should not short-circuit during the procedure. The tissue will typically decrease in thickness when electrosurgical current is applied, thereby allowing the seal surfaces to move closer together. This decrease in thickness should not result in the electrodes making direct contact with each other. Otherwise, a short circuit could give the electrosurgical current a preferential path around the tissue and may result in a poor seal.

BRIEF DESCRIPTION OF THE DRAWINGS

FIG. 1' is a schematic diagram of an electrosurgical vessel sealing system.

FIG. 2' is a set of power curves which represent the electrosurgical power delivered to the tissue as a function of the tissue impedance.

FIG. 4 is a schematic plan view of an alternative embodiment of an instrument for vessel fusion having a shorter curved jaw.

FIG. 5 is side view of the instrument shown in FIG. 4.

FIG. 6 is a schematic plan view of an alternative embodiment of an instrument for vessel fusion having a straight jaw.

FIG. 7 is a side view of the instrument shown in FIG. 7.

DETAILED DESCRIPTION OF THE INVENTION

Figure 1:
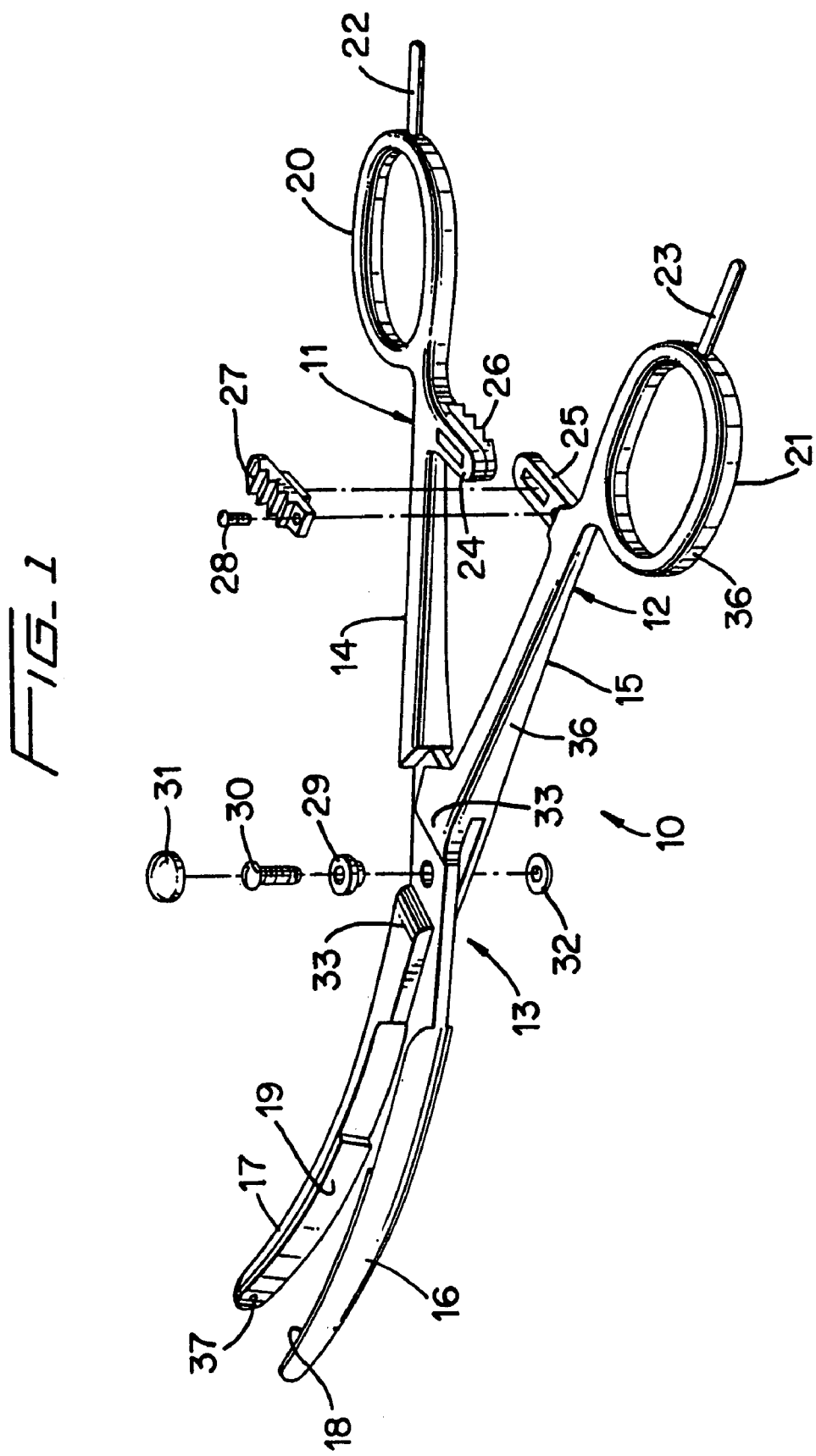
FIG. 1 is a perspective view of a bipolar instrument for vessel fusion, shown partially exploded.

Referring to FIG. 1, the instrument 10 has an inner member 11 and an outer member 12. The members 11 and 12 are connected through an open lockbox 13 which has a gap between flanges 33. The terms "inner" and "outer" are used to distinguish the members 11 and 12, and their component parts, according to the members' respective positions at the open lockbox 13. The inner member 11 is fitted generally within the inner surfaces of the open lockbox 13 and is captured by the flanges 33. The outer member generally forms the outside surfaces of the open lockbox 13.

The inner member 11 has an inner shank 14, an inner jaw 16, and an inner ring handle 20. Similarly, the outer member 12 has an outer shank 15, an outer jaw 17, and an outer ring handle 21. The ring handles, 20 and 21, are designed for a surgeon to hold and manipulate the instrument 10. The jaws, 16 and 17, are designed to grasp tissue between the opposing seal surfaces 18 and 19.

Each shank, 14 and 15, has a respective ratchet stub 24 or 25. Ratchet teeth, 26 and 27, are designed to interlock in a manner that hold the members, 11 and 12, in position. The shanks 14 and 15 are deflected in the manner of a cantilever spring when the jaws are forced together by the surgeon. The deflection of the shanks 14 and 15 produces a spring restoring force that can be opposed by interlocking the ratchet teeth, 26 and 27.

The instrument 10 does not cause a short circuit when the ratchet teeth, 26 and 27, are interlocked. This is accomplished by a suitable selection and placement of electrically insulating materials. In the preferred embodiment, the ratchet teeth 26 and 27 are composed of a polymeric material which is press-fit into the ratchet stubs 24 and 25. A ratchet screw 28 is used in the preferred embodiment to secure the ratchet teeth 26 and 27 into the ratchet stubs 24 and 25. During manufacture, the ratchet teeth 26 and 27 may be formed from a blank after the blank has been press fit into the ratchet stubs 24 and 25.

In a second embodiment, one of the members, 11 or 12, includes the ratchet stub and ratchet teeth as in integral part of the member, while the other member, 12 or 11, has an insulative layer that prevents a short circuit between the members 11 and 12 when the ratchets are engaged.

The open lockbox 13 has the function of providing a pivoting joint for the members 11 and 12. In addition, the flanges 33 provide lateral support to help maintain alignment of the jaws 16 and 17. Closed lockbox designs are typically used in standard hemostat designs, wherein an inner member is completely captured through a slot in an outer member. The open lockbox 13 in present invention has a gap between the flanges 33 that is different from a closed lockbox design. The gap in the open lockbox 13 provides convenient access to install an electrically insulated pivot.

The electrically insulated pivot in the present invention comprises a shoulder washer 29 supporting a lockbox screw 30. The shoulder washer 29 is composed of an electrically insulative material that prevents a short circuit between the members 11 and 12. A large screw cap 31 fits over the head of the lockbox screw 30. A small screw cap 32 fits over the threaded end of the lockbox screw 30.

Each member 11 and 12 is connected to a pole of a bipolar electrosurgical generator. Electrical connectors 22 and 23 are located on the ring handles 20 and 21 to provide a convenient point of connection. The members 11 and 12 are formed of an electrically conductive material, such as stainless steel. The exposed surfaces of the members, except for the connectors 22 and 23 and the seal surfaces 18 and 19, are preferably spray coated with an insulating material.

The characteristics of the bipolar electrosurgical current are determined by the design of the electrosurgical generator. In the preferred embodiment, the generator will have an output wherein the peak-to-peak voltage will not exceed 130 Volts. This is because higher voltages can cause sparking which results in localized burning of tissue which may result in a failure of the tissue weld. The preferred embodiment has the generator capable of producing high frequency output current of at least 2 Amps RMS. High electrical current is important because it heats the tissue sufficiently to melt the collagen. Lower electrical currents will often produce weak tissue welds with low bursting strength.

During operation, the instrument 10 is used to grasp tissue between the seal surfaces 18 and 19. The surgeon squeezes the ring handles 20 and 21 together, causing pressure to be applied to the tissue. The ratchet teeth 26 and 27 are interlocked at the appropriate ratchet setting, depending on the tissue type and tissue thickness. Bipolar electrosurgical current is applied through the instrument and the tissue to cause the tissue to fuse.

The jaws 16 and 17 have a structure and cross-section that resist bending under load. Thus, for purposes of engineering analysis, the shank portions 14 and 15 act as a cantilever supported beam once the seal surfaces 18 and 19 have been mated. The length of this idealized cantilever beam extends from the lockbox screw 30 to the location of the respective ratchet subs 24 or 25. It is possible to model each shank as a cantilever spring having a spring constant. Each ratchet position is designed to transmit a particular closure force to the jaws 16 and 17 against the action of the restoring force of the cantilever spring.

The spring constant is generally a function of Young's Modulus of the shank material, the moment of inertia of the shank, and the length of the shank portion 14 and 15. When the jaws 16 and 17 of the instrument 10 are closed together, each shank 14 and 15 approximates a cantilever-supported beam. It is properly assumed that the deflection of each shank 14 and 15 remains within the linear range of its stress-strain curve. The behavior of such a beam is well known to materials engineers. A large spring constant will result in large closure forces between the seal surfaces 18 and 19. Similarly, a small spring constant will result in a small closure forces between the seal surfaces 18 and 19. The choice of a proper spring constant will depend on the length of the shank 14 or 15 and the distance between ratchet stops 26 and 27.

Experimental results in animal studies suggest that the magnitude of pressure exerted on the tissue by the seal surfaces 18 and 19 is important in assuring a proper surgical outcome. Tissue pressures within a working range of 7 $kg/cm^2$ to 13 $kg/cm^2$ have been shown to be effective for sealing arteries and vascular bundles. It is desirable to tune the spring constant of the shank portions 14 and 15, in conjunction with the placement of the ratchet teeth 26 and 27, such that successive ratchet positions will yield pressures within the working range. In one embodiment, the successive ratchet positions are two millimeters apart.

Pressure on the tissue can be described in several ways. Engineers will recognize that the amount of pressure exerted on the tissue depends on the surface area of the tissue that is in contact with the seal surfaces. In the one embodiment, the width of each seal surface 18 and 19 is in the range of 2 to 5 millimeters, and preferably 4 millimeters width, while the length of each seal surface 18 and 19 is preferably in the range of 10 to 30 millimeters. It has been found through experimentation that at least one interlocking ratchet position preferably holds the closure force between approximately 400 and 650 grams per millimeter of seal surface width. For example, if the width of the seal surface 18 and 19 is 4 millimeters, the closure force is preferably in the range of 1600 grams to 2600 grams. In one embodiment, the closure force is 525 grams per millimeter of width, yielding a closure force of 2100 grams for a 4 millimeter width seal surface 18 and 19.

It has been found experimentally that local current concentrations can result in an uneven tissue effect, and to reduce the possibility of this outcome, each seal surface 18 and 19 has a radiused edge in the preferred embodiment. In addition, a tapered seal surface 18 and 19 has been shown to be advantageous in certain embodiments because the taper allows for a relatively constant pressure on the tissue along the length of the seal surfaces 18 and 19. The width of the seal surfaces 18 and 19 is adjusted, in certain embodiments, wherein the closure force divided by the width is approximately constant along the length.

In one embodiment, a stop 37, made from insulative material, is located in the instrument to maintain a minimum separation of at least 0.3 millimeters between the seal surfaces 18 and 19, as shown in FIG. 1. The stop 37 reduces the possibility of short circuits between the seal surfaces 18 and 19.

Figure 11A:
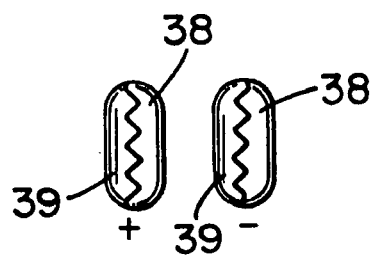
FIG. 11 is a top view each of a pair of seal surfaces showing conductive regions and insulative regions that prevent a short circuit when the seal surfaces are mated in opposition.
Figure 11B:

In certain embodiments, as shown in FIGS. 11A and 11B, the seal surfaces 18 and 19 comprise conductive regions 38 and insulative regions 39 arranged such that each conductive region 38 opposes an insulative region 39 when the opposable seal surfaces 18 and 19 are mated in opposition. The seal surfaces 18 and 19, in certain embodiments, may be removable from its respective member 11 or 12 by standard mechanical interfaces, such as a pin and socket arrangement.

Figure 2:
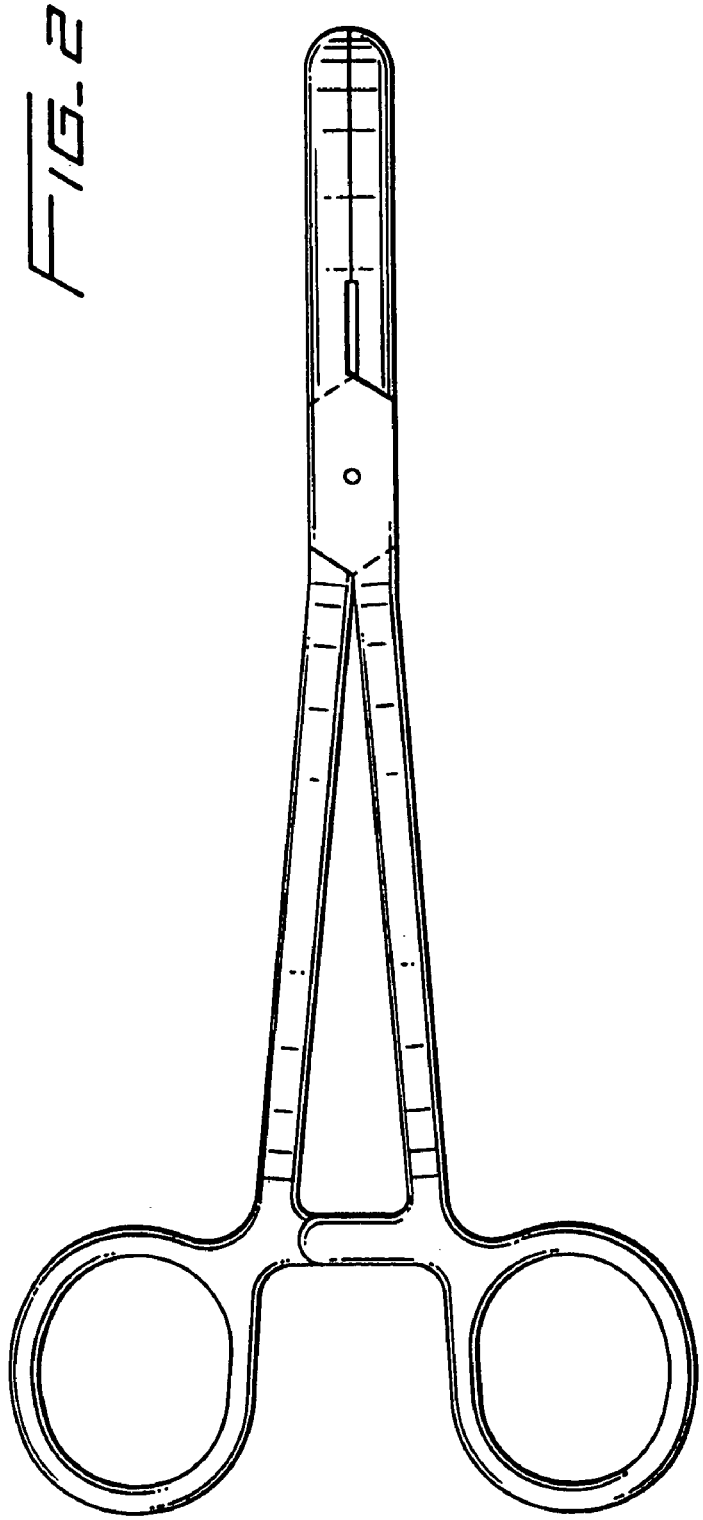
FIG. 2 is a schematic plan view of a bipolar instrument for vessel fusion having a longer curved jaw.
Figure 3:
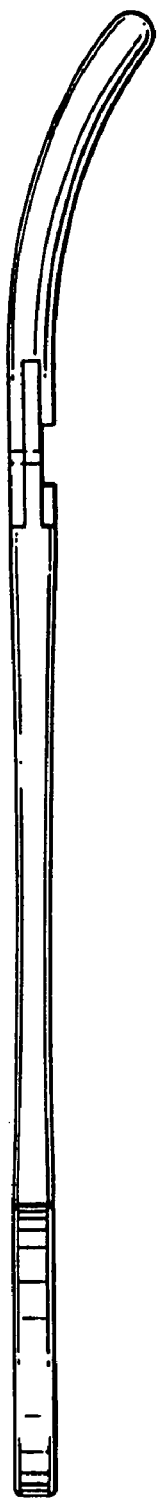
FIG. 3 is a side view of the instrument shown in FIG. 2.
Figure 2:
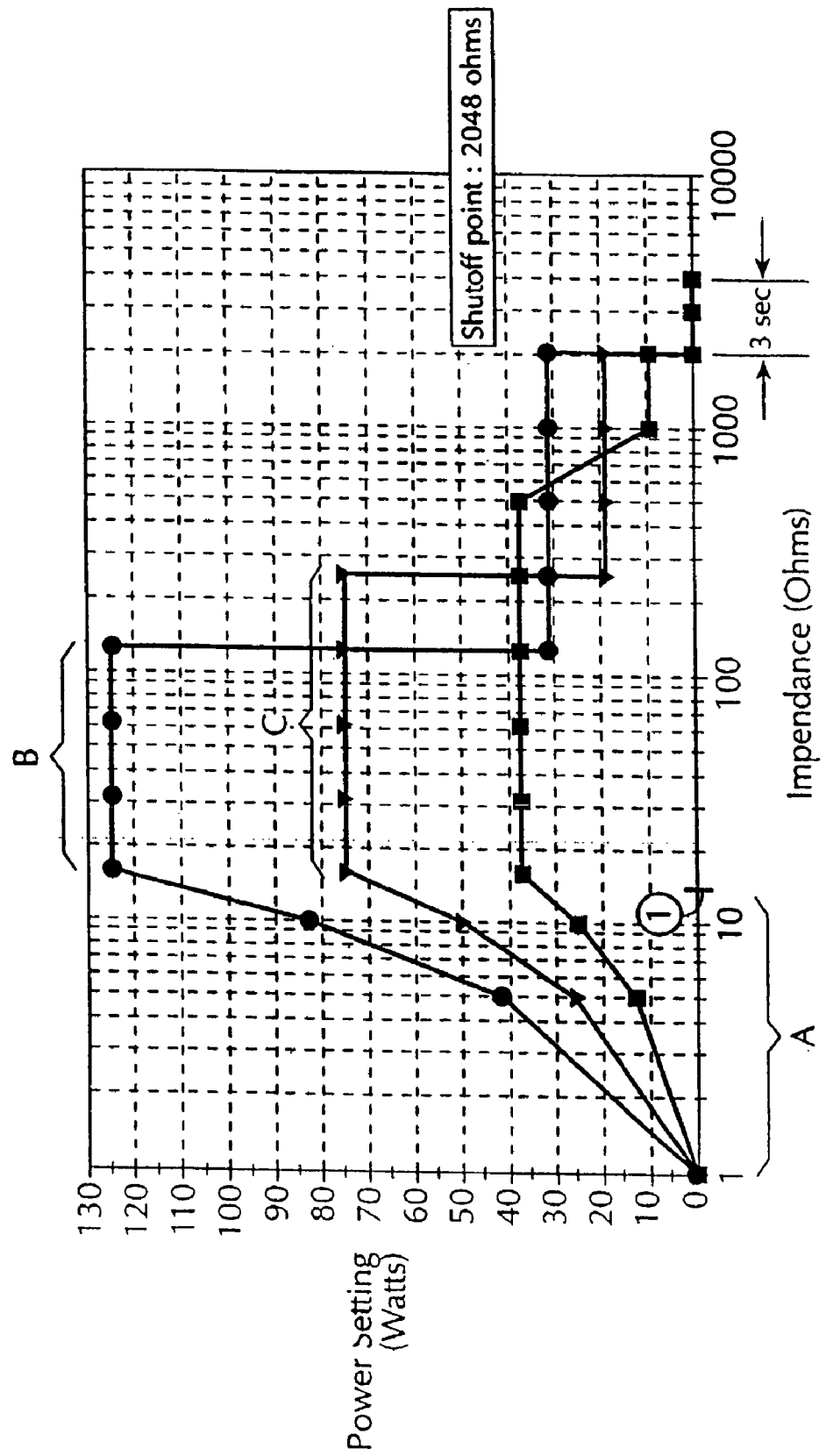

FIG. 2 shows an embodiment for a thirty-two millimeter curved seal surface. FIG. 3 is a side view of FIG. 2. The members 11 and 12 in FIG. 2 are formed from American Iron and Steel Institute (AISI) 410 stainless steel. The length and cross sectional area of the shank portions 14 and 15 are shown in FIGS. 2 and 3 to provide a spring constant of twenty-five pounds per inch deflection.

The embodiment shown in FIGS. 4 and 5 has a twenty millimeter curved seal surface. The embodiment shown in FIGS. 6 and 7 has a thirty-two millimeter straight seal surface. Each embodiment in FIGS. 2 through 7 is designed to have the look and feel of a standard hemostat.

Figure 8:
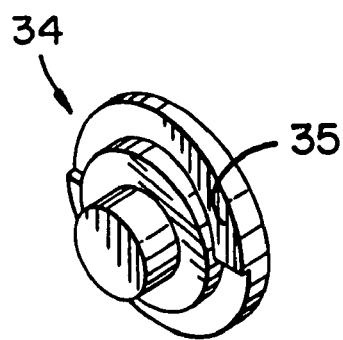
FIG. 8 is a perspective view of a shoulder pin.
Figure 9:
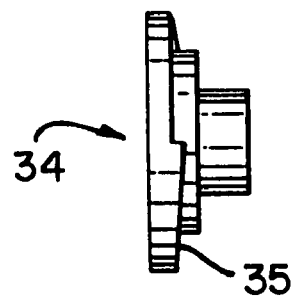
FIG. 9 is a side view of a shoulder pin.
Figure 10:
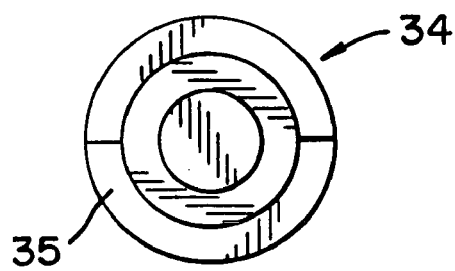
FIG. 10 is a front view of a shoulder pin.

FIGS. 8, 9 and 10 show three views of a shoulder pin 34 that can be used, in certain embodiments, instead of the lockbox screw 30 to connect the members 11 and 12. The shoulder pin 34 has at least one ramp surface 35 that engages one of the members 11 or 12 to cause increasing mechanical interference as the jaws 16 and 17 move toward each other. In one embodiment, the shoulder pin 34 forms part of the open lockbox 13 to aid alignment of the seal surfaces 18 and 19. In another embodiment, the shoulder pin 34 is used without an open-lockbox 13, and movably pins the members 11 and 12 together without a flange 33. The interference fit may require the calibration of the instrument 10 to insure that the applied force will be sufficient to provide the appropriate working pressure between the seal surfaces 18 and 19. A slightly higher spring constant in the shank portions 14 and 15 is preferably used, depending on the level of interference caused by the shoulder pin.

A method of using the bipolar electrosurgical instrument comprises the following steps. A surgeon grasps the ring handles 20 and 21 on the instrument 10 to manipulate the jaws 16 and 17. A vessel or vascular tissue is compressed between the opposable seal surfaces 18 and 19. The opposable seal surfaces 18 and 19 preferably come together in aligned opposition due to the alignment action of the open-lockbox 13, or in certain embodiments due to the alignment action of the shoulder pin 34. The surgeon further deflects the shank portions 14 and 15 of the members 11 and 12 to engage the ratchet teeth 26 and 27. The engagement of the ratchet teeth 26 and 27 hold the shank portions 14 and 15 in their deflected positions to provide a constant spring force that is transmitted as a closure force to the jaws 16 and 17. An electrosurgical generator is connected to the instrument 10 through connectors 22 and 23 on the ring handles 20 and 21. An electrical switch is used to close a circuit between the generator and the instrument 10. The switch may be a footswitch such as Valleylab's catalog number E6009, available from Valleylab Inc., Boulder Colo. The electrosurgical current flows through an electrically conductive path on each of the inner and outer members 11 and 12 between its respective electrical connector, 22 or 23, and its respective seal surface, 18 or 19. An electrically insulative coating 36 substantially covers each member 11 and 12, except for the seal surfaces 18 and 19, to protect the surgeon against electrical arcs.

It is to be understood that the above described embodiments are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. An electrosurgical system, comprising:
    an electrosurgical generator for generating electrosurgical energy;
    a first shaft having a jaw member attached to a distal end thereof, a second shaft having a jaw member attached to a distal end thereof, the first and second jaw members each including a sealing surface disposed thereon which reside in opposing relation relative to one another, the jaw members being movable from a first position wherein the sealing surfaces are disposed in spaced apart relation relative to one another to at least one second position wherein the sealing surfaces grasp tissue therebetween;
    a connector adapted to electrically couple the jaw members to a source of electrosurgical energy such that the sealing surfaces are capable of conducting electrosurgical energy through tissue held therebetween;
    a ratchet operatively associated with at least one of the shafts, the ratchet being selectively positionable to maintain to a closure pressure in the range of about 7 kg/cm$^2$ to about 13 kg/cm$^2$ between sealing surfaces; and
    regulating means being configured to monitor the phase angle between the output voltage and the current emanating from the electrosurgical generator and terminate the electrosurgical energy once the phase angle reaches a predetermined angle.

2. An electrosurgical system according to claim 1 wherein the regulating means includes a feedback control system disposed within the generator.

3. An electrosurgical system according to claim 1 wherein the regulating means is further configured to monitor the impedance on the electrosurgical generator and terminate the electrosurgical energy once the impedance reaches a predetermined level.

4. An electrosurgical system according to claim 3 wherein the predetermined level is above 1000 ohms.

5. An electrosurgical system according to claim 1 wherein the predetermined angle is greater than about 50 degrees.

* * * * *